United States Patent
Schmelz et al.

(10) Patent No.: US 8,608,809 B2
(45) Date of Patent: Dec. 17, 2013

(54) STABLE OXIDATIVE COLOURING COMPOSITION FOR KERATIN FIBRES

(75) Inventors: Sandra Schmelz, Marktheidenfeld (DE); Jürgen Ehmig, Riedstadt (DE)

(73) Assignee: Kao Germany GmbH, Darmstadt (DE)

( * ) Notice: Subject to any disclaimer, the term of this patent is extended or adjusted under 35 U.S.C. 154(b) by 0 days.

(21) Appl. No.: 13/818,164

(22) PCT Filed: Aug. 16, 2011

(86) PCT No.: PCT/EP2011/064104
§ 371 (c)(1),
(2), (4) Date: Mar. 25, 2013

(87) PCT Pub. No.: WO2012/025435
PCT Pub. Date: Mar. 1, 2012

(65) Prior Publication Data
US 2013/0180058 A1    Jul. 18, 2013

(30) Foreign Application Priority Data
Aug. 24, 2010 (EP) .................. 10008793

(51) Int. Cl.
*A61Q 5/10* (2006.01)
(52) U.S. Cl.
USPC ............. 8/405; 8/406; 8/408; 8/435; 8/587; 8/111
(58) Field of Classification Search
USPC ............ 8/405, 406, 408, 435, 587, 111
See application file for complete search history.

(56) References Cited

U.S. PATENT DOCUMENTS

| 4,295,848 A | 10/1981 | Grollier et al. |
| 2003/0106166 A1 | 6/2003 | Mitamura et al. |
| 2009/0019645 A1* | 1/2009 | Plos .................. 8/405 |

FOREIGN PATENT DOCUMENTS

| AT | 238 375 B | 2/1965 |
| DE | 150 694 | 9/1981 |
| EP | 1 714 637 A2 | 10/2006 |
| EP | 1 719 498 A1 | 11/2008 |
| EP | 2 422 762 A1 | 2/2012 |
| JP | 53 059041 A | 5/1978 |
| JP | 2003 081791 A | 3/2003 |
| WO | 2008/020730 A1 | 2/2008 |

OTHER PUBLICATIONS

International Preliminary Report on Patentability dated Apr. 9, 2013.
International Search Report mailed Mar. 25, 2013.
Grad Baume, Wikipedia, Jan. 10, 2013, Retrieved from the internet: URL:http://de.wikipedia.org/wiki/Grad_Baum%C3%A9 [retrieved on Jan. 28, 2013].

* cited by examiner

*Primary Examiner* — Eisa Elhilo
(74) *Attorney, Agent, or Firm* — Norris McLaughlin & Marcus P.A.

(57) ABSTRACT

An oxidative dyeing composition comprises at least one oxidative dye precursor comprising further at least two structurally different reducing agents wherein the first is selected from inorganic reducing agents and present at a concentration of at least 0.1% by weight calculated to the total composition, and the second is an organic reducing agent and/or its salts selected from thioglycolic acid, acetylcysteine and cysteine, and their salts, wherein the composition is substantially free of ascorbic acid and/or its salts.

13 Claims, No Drawings

STABLE OXIDATIVE COLOURING COMPOSITION FOR KERATIN FIBRES

This application is a 371 application of PCT/EP2011/064104 filed Aug. 16, 2011, which claims foreign priority benefit under 35 U.S.C. §119 of European Application No. 10008793.1 filed Aug. 24, 2010.

Present invention relates to a stable oxidative colouring composition for keratin fibres.

Oxidative colouring compositions have been produced under substantially oxygen free atmosphere and also stored under substantially oxygen free conditions in order to guarantee the stability against oxidation during shelf life. Besides that for minimizing any risk of oxidative destruction of the precursors, antioxidants, practically being reducing agents, have been formulated mostly together with additional free radical scavengers. Most commonly used antioxidant is sodium sulphite and most commonly used free radical scavenger is ascorbic acid and its salts such as sodium salt. It should be noted that ascorbic acid and its salts are on one hand known with their free radical scavenging activity and on the other hand, known because of their antioxidant effect. Although it may finally end up at the same effect, the two mechanisms, anti-oxidation and radical scavenging, are distinctive from each other.

Attempts have been made to find out alternatives to the above combination, but so far failed because of being ineffective. The simple idea of using sodium sulfite alone at a higher concentration does not result in the prevention of oxidative destruction of the precursors.

The aim of the inventors has been to find out an antioxidant system which is alternative to the sodium sulphite-ascorbic acid and/or its salts combination. It is furthermore the aim of the present invention that using the antioxidant system of the present invention, intensive oxidative colouration is achieved after storing said composition for a substantially long period of time.

Present inventors have surprisingly found out that a combination of an inorganic reducing agent and an organic reducing agent other than ascorbic acid and its salts is as effective as at present commonly used combination and even after a long storage period of time intensive colours are achieved which does not deviate from initial colours significantly.

Accordingly, the first object of the present invention is an oxidative dyeing composition comprising at least one oxidative dye precursor comprising further at least two structurally different reducing agents wherein the first is selected from inorganic reducing agents and present at a concentration of at least 0.1% by weight calculated to the total composition, and the second is an organic reducing agent and/or its salts selected from thioglycolic acid and its salts such as ammonium thioglycolate, ethanolamine thioglycolate, sodium thioglycolate, potassium thioglycolate, magnesium thioglycolate and strontium thioglycolate, acetylcysteine and its salts such as hydrochloride salt, thioglycerine and cysteine and its salts such as cysteine hydrochloride and their mixtures, wherein the composition is substantially free of ascorbic acid and/or its salts, wherein the total concentration of inorganic and organic reducing agents does not exceed 5% by weight calculated to the total composition.

The second object of the present invention is method of stabilizing oxidative dyeing composition comprising at least one oxidative dye precursor wherein the composition comprises further at least two structurally different reducing agents wherein the first is selected from inorganic reducing agents and present at a concentration of at least 0.1% by weight calculated to the total composition, and the second is an organic reducing agent and/or its salts selected from thioglycolic acid and its salts such as ammonium thioglycolate, ethanolamine thioglycolate, sodium thioglycolate, potassium thioglycolate, magnesium thioglycolate and strontium thioglycolate, acetylcysteine and its salts such as hydrochloride salt, thioglycerine and cysteine and its salts such as cysteine hydrochloride and their mixtures, wherein the composition is substantially free of ascorbic acid and/or its salts, wherein the total concentration of inorganic and organic reducing agents does not exceed 5% by weight calculated to the total composition.

The third object of the present invention is method of stabilizing oxidation sensitive composition wherein the composition is added at least two structurally different reducing agents wherein the first is selected from inorganic reducing agents and present at a concentration of at least 0.1% by weight calculated to the total composition, and the second is an organic reducing agent and/or its salts selected from thioglycolic acid and its salts such as ammonium thioglycolate, ethanolamine thioglycolate, sodium thioglycolate, potassium thioglycolate, magnesium thioglycolate and strontium thioglycolate, acetylcysteine and its salts such as hydrochloride salt, thioglycerine and cysteine and its salts such as cysteine hydrochloride and their mixtures, wherein the composition is substantially free of ascorbic acid and/or its salts, wherein the total concentration of inorganic and organic reducing agents does not exceed 5% by weight calculated to the total composition.

Oxidative dyeing composition of the present invention is based on at least one oxidative dyeing precursor. In principle any oxidative dyeing precursor known in the field of oxidative colouring is suitable for composition of the present invention. Some of them as examples are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylenediamine, 2-(2,5-diaminophenyl)ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and 1,2,4-triamino benzene, or the water-soluble salts thereof.

Total concentration of oxidative dye precursors is in the range of 0.01 to 10% by weight, preferably 0.05 to 7.5% by weight and more preferably 0.1 to 5% by weight, calculated to total composition.

The composition according to the invention preferably comprises one or more coupling substances. Suitable ones are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxypyridine, 1,3-bis(2,4-diaminophenoxy) propane and/or its respective salts 2-dimethyl-amino-5-aminopyridine, 2,6-diaminopyridine, 5-amino-2-methylphenol, 2-methyl-5-hydroxyethylaminophenol, 2-methyl-5-amino-6-chlorphenol, 2-bis(2-hydroxyethyl)aminotoluene, 2-amino-5-methylphenol,α-naphthol, 4,6-dichlororesorcinol, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxybenzene, 5-amino-2-methoxyphenol, hydroxybenzomorpholine, 1,2,4-trihydroxybenzene, phenylmethylpyrazolone, 3-amino-2,4-dichlorophenol, hydroxyethyl-3,4-methylenedioxyaniline, 2.6-dimethoxy-3,5-dimethylpyridine, 5-amino-4-chloro-2-methylphenol, hydroxypropyl-bis-(N-hydroxyethyl-p-phenylenediamine), 1-acetoxy-2-methylnaphthalene, 2,2'-methylenebis-4-aminophenol and/or or their respective salts.

Total concentration of one or more coupling agent is in the range of 0.001 to 5% by weight, preferably 0.005 to 3% by weight and more preferably 0.01 to 2.5% by weight, calculated to total composition.

Composition of the present invention may further comprise one or more direct dyes. Direct dyes are found to be useful for adjusting colour tone within the meaning of the present invention.

Direct dyes suitable are cationic, anionic and/or nitro dyes. Suitable non-limiting examples to cationic ones are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Suitable non-limiting examples to anionic ones are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Suitable non-limiting examples to nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid. Preferred direct dyes are the nitro dyes.

Total concentration of one or more direct dyes is in the range of 0.001 to 10% by weight calculated to total composition.

Composition of the present invention comprises at least one inorganic reducing agent at a concentration of at least 0.1% by weight calculated to total composition. Suitable inorganic reducing agents are ammonium bisulfite, ammonium sulfite, potassium metabisulfite, potassium sulfite, sodium hydrosulfite, sodium metabisulfite and sodium sulfite. The most preferred inorganic reducing agent is sodium sulfite. It should be noted that the compositions may comprise more than one inorganic reducing agent. Therefore, mixtures of any inorganic reducing agent are also suitable for the compositions of the present invention.

Total concentration of inorganic reducing agent(s) is in the range of 0.1 to 2.5% by weight, preferably 0.2 to 2% by weight and more preferably 0.25 to 1.5% by weight, calculated to total composition prior to mixing with an oxidizing agent.

Composition of the present invention comprises at least one organic reducing agent. Suitable organic reducing agents are thioglycolic acid and its salts such as ammonium thioglycolate, ethanolamine thioglycolate, sodium thioglycolate, potassium thioglycolate, magnesium thioglycolate and strontium thioglycolate, acetylcysteine and its salts such as hydrochloride salt, thioglycerine and cysteine and its salts such as cysteine hydrochloride. More preferred organic reducing agents are cysteine and its derivatives and the most preferred is acetylcysteine and its salts. It should be noted that the compositions may comprise more than one organic reducing agent. Therefore, mixtures of any inorganic reducing agent are also suitable for the compositions of the present invention.

Total concentration of organic agent(s) is in the range of 0.1 to 2.5% by weight, preferably 0.2 to 2% by weight and more preferably 0.25 to 1.5% by weight, calculated to total composition prior to mixing with an oxidizing agent.

It has further been found out that the weight ratio of the inorganic and organic reducing agents may play a role in stabilizing the oxidative dyeing compositions. Therefore, preferably the weight ratio of inorganic reducing agent to organic reducing agent is in the range of 20:1 to 1:5, preferably 10:1 to 1:2, more preferably 7:1 to 1:1.5 and most preferably 5:1 to 1:1.

Composition of the present invention is mixed prior to application onto hair with a composition comprising at least one oxidizing agent. The preferred oxidizing agent is hydrogen peroxide at a concentration of 0.5 to 12% by weight calculated to the total composition. Other peroxides such as urea peroxide, melanin peroxide and sodium bromate are also possible to use.

Therefore, further object of the present invention is process for colouring keratin fibres especially human hair wherein a composition comprising at least one oxidative dye precursor comprising further at least two structurally different reducing agents wherein the first is selected from inorganic reducing agents and present at a concentration of at least 0.1% by weight calculated to the total composition, and the second is an organic reducing agent and/or its salts selected from thioglycolic acid and its salts such as ammonium thioglycolate, ethanolamine thioglycolate, sodium thioglycolate, potassium thioglycolate, magnesium thioglycolate and strontium thioglycolate, acetylcysteine and its salts such as hydrochloride salt, thioglycerine and cysteine and its salts such as cysteine hydrochloride and their mixtures, wherein the composition is substantially free of ascorbic acid and/or its salts, wherein the total concentration of inorganic and organic reducing agents does not exceed 5% by weight calculated to the total composition, is mixed with an oxidizing composition comprising at least one oxidizing agent and is applied onto hair and is processed for 1 to 45 min at a temperature of 20 to 45° C. and rinsed off from hair.

The mixing ratio of the composition comprising at least one oxidative dye precursor comprising further at least two structurally different reducing agents wherein the first is selected from inorganic reducing agents and present at a concentration of at least 0.1% by weight calculated to the total composition, and the second is an organic reducing agent and/or its salts selected from thioglycolic acid and its salts such as ammonium thioglycolate, ethanolamine thioglycolate, sodium thioglycolate, potassium thioglycolate, magnesium thioglycolate and strontium thioglycolate, acetylcysteine and its salts such as hydrochloride salt, thioglycerine and cysteine and its salts such as cysteine hydrochloride and their mixtures, wherein the composition is substantially free of ascorbic acid and/or its salts, wherein the total concentration of inorganic and organic reducing agents does not exceed 5% by weight calculated to the total composition and oxidizing composition comprising at least one oxidizing agent is preferably in the range of 3:1 to 1:3, by weight, more preferably in the range of 2:1 to 1:2, by weight, and in particular 1:1, by weight.

In the best way, the composition of the present invention is provided to the consumers as a kit which should include all parts required for colouring hair. Therefore, another object of the resent invention is kit for oxidative colouring hair comprising at least two compositions wherein the one is an oxidative dyeing composition comprising at least one oxidative dye precursor comprising further at least two structurally different reducing agents wherein the first is selected from inorganic reducing agents and present at a concentration of at least 0.1% by weight calculated to the total composition, and the second is an organic reducing agent and/or its salts selected from thioglycolic acid and its salts such as ammonium thioglycolate, ethanolamine thioglycolate, sodium thioglycolate, potassium thioglycolate, magnesium thioglycolate and strontium thioglycolate, acetylcysteine and its salts such as hydrochloride salt, thioglycerine and cysteine and its salts such as cysteine hydrochloride and their mixtures, wherein the composition is substantially free of ascorbic acid and/or its salts, wherein the total concentration of inorganic and organic reducing agents does not exceed 5% by weight calculated to the total composition, and the other is a composition comprising at least one oxidizing agent.

pH of the composition is in the range of 5 to 12, preferably 6 to 11 and more preferably 6.8 to 10, after mixing with an oxidizing agent.

In the most preferred embodiment of the present invention composition comprises only two reducing agents as disclosed above and does not comprise any other reducing agents.

Composition of the present invention can comprise additionally substances customarily found in colouring compositions.

Compositions of the present invention can be in the form of solutions, dispersions, gels and emulsions. Most preferred is emulsion.

Colouring composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition. Non-limiting examples are myristic acid, palmitic acid, behenic acid, steraic acid, oleic acid, linoleic acid. The most preferred fatty acid is oleic acid.

Colouring composition of the present invention comprise at least one fatty alcohol or mixture of fatty alcohols with the chain length of 14 to 22 C atoms which may be straight or branched, saturated or unsaturated. Examples to suitable fatty alcohols, without limiting the choice, are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O or as Lanette N in mixture with sodium cetearyl sulfate from Cognis. Total fatty alcohol content should be in the range of 1 to 20% by weight, calculated to total composition.

Colouring compositions according to present invention comprises surfactants selected from anionic, amphoteric (or zwiterionic) and/or cationic surfactants as emulsifier or solubilizer. Cationic surfactants are as well used as hair conditioners in the colouring composition.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, seteareth-30, palmeth-20, steareth-20, beheneth-20 etc. These compounds are named according to the fatty alcohol they are originating and number of ethoxyl groups is given at the end. These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula $$R_6-O-(R_3O)_n-Z_x,$$

wherein $R_6$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Anionic surfactants suitable within the scope of the invention are in principal known from the cleansing compositions and may be present in an amount from 0.1 to about 10% by weight, calculated to the total composition prior to mixing with an oxidizing agent. Compatibility of anionic surfactant in the composition should be taken into account when choosing the type and the concentration.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride(ether)sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are a-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

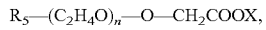

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

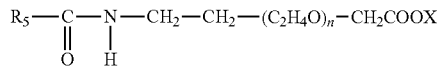

wherein $R_5$ and X have the above meanings, and n is in particular a number from 1 to 10, preferably 2.5 to 5.

Such products have been known for some time and are on the market, for example, under the trade name "AKYPO®" and "AKYPO-SOFT®". Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants in a mixture.

An overview of the anionic surfactants suitable for the present invention can furthermore be found in the monography of K. Schrader, "Grundlagen and Rezepturen der Kosmetika", 2$^{nd}$ Ed. (1989, Hüthig Buchverlag), pp. 595-600 and pp. 683 to 691.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Colouring composition can comprise cationic surfactants as emulsifier, solubilizer and/or conditioning ingredients according to the formula,

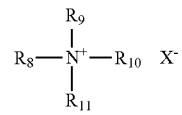

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 1-4 or

where $R_{13}$ is saturated or unsaturated, branched or non-branched alkyl chain with 7-21 C atoms and n has typical value of 1-4, and $R_9$ is unsaturated or saturated, branched or non-branched alkyl chain with 1-22 C atoms or

or

where $R_{12}$, $R_{13}$ and n are same as above.

$R_{10}$ and $R_{11}$ are lower alkyl chain with 1 to 4 C atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Form the above mentioned surfactants preferred are non-ionic and anionic surfactants and their mixtures.

Total surfactant concentration is in the range of 0.5 to 15%, preferably 1 to 10%, more preferably 1 to 7.5% by weight calculated to total composition prior to mixing with an oxidizing agent.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46. Among those the most preferred one is the Polyquaternium 11 as well known with its trade name Gafquat from ISP and as Luviquat PQ from BASF.

Typical concentration range for any of the cationic conditioners mentioned above can be 0.01-5% by weight, preferably 0.03-2.5% by weight and more preferably 0.05-1.5% by weight, calculated to total composition.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

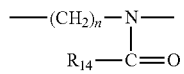

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

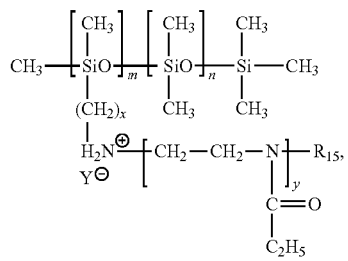

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Colouring compositions according to the present invention can contain organic solvents as penetration enhancers and also as a solubilzer. Examples of such organic solvents are benzyloxy ethanol, benzyl alcohol, phenoxy ethanol, phenoxy isopropanol, methyl phenoxy ethanol, benzyl glycerol, N-benzyl formide, N-methyl pyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 20%, preferably 0.5-15%, more preferably 0.5-10%, by weight calculated to the total composition.

Colouring compositions according to the invention may comprise thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition.

Optionally, the colouring composition of this invention can comprise further hair conditioning agents such as silicone oils either volatile or non-volatile, natural and synthetic oils.

Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Additional non-ionic conditioning agents may be polyols such as glycerin, glycol and derivatives, polyethyleneglycoles known with trade names Carbowax PEG from Union Carbide and Polyox WSR range from Amerchol, polyglycerin and polyethyleneglycol mono or di fatty acid esters.

Compositions may further comprise at least one ubiquinone of the formula

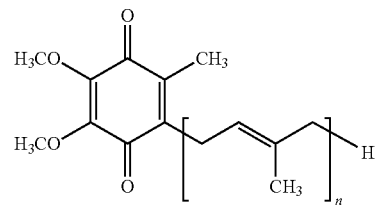

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition.

The composition comprises ubiquinone which is preferably selected from the ones where n is a number between 6 and 10 and more preferably it is ubichinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition.

Suitable amino acids are glycin, histidine, citrullin, asparagine, alanin, valin, leucin, isoleucin, pyrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrolin, serine, tyrosine, threonine and gluatamine. More preferably, at least one amino acid is selected from glycin, histidine, asparagine, alanin, valin, leucin, pyrolin, serine, tyrosine and gluatamine, and most preferably at least one amino acid is selected from glycin, asparagine, alanin, valin, leucin, and serine.

Composition can comprise further ceramide type of compound with the general formula

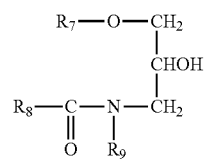

where $R_7$ and $R_8$ are independent from each other alkyl- or alkenyl group with 10 to 22 carbon atoms, $R_9$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Composition can comprise at least one diamine compound. Preferred diamide compounds are according to the general structure

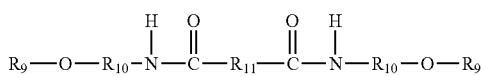

wherein $R_9$ is a linear or branched, saturated or unsaturated alkyl chain with 1 to 12 C atoms which may be substituted with hydroxy and/or alkoxy groups, preferably $R_9$ is linear or branched, saturated or unsaturated alkyl chain with 1 to 12 C atoms which may be substituted by 1 to 3 substituents selected from a hydroxy group and C1 to C6 alkoxy group, more preferably $R_9$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{10}$ is linear or branched alkyl chain with 1 to 5 C atoms, preferably linear or branched alkyl chain with 2 to 5 C atoms and more preferably an alkyl chain with 2 to 3 C atoms, and $R_{11}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

(A)
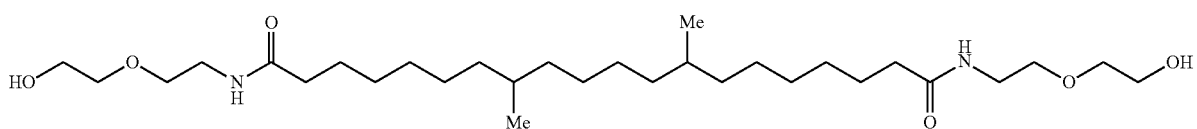

(B)
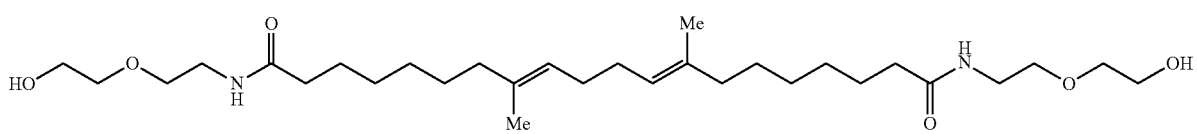

(C)
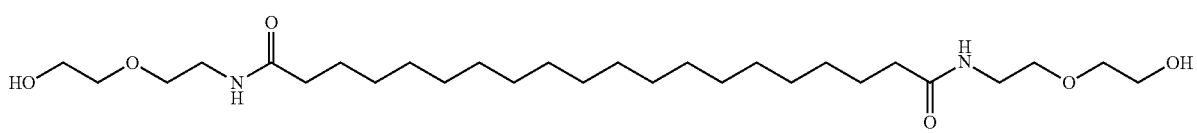

(D)
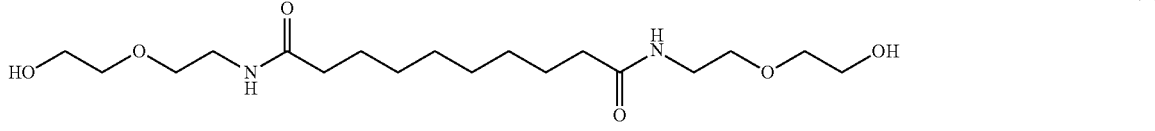

(E)
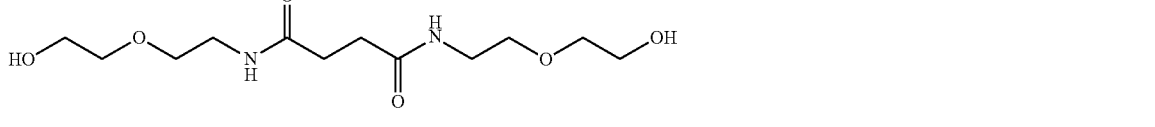

(F)
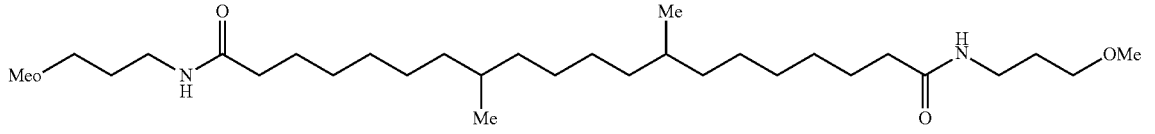

(G)
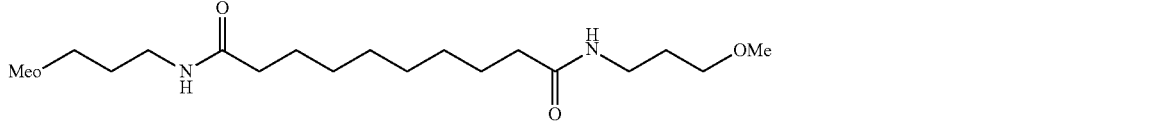

Particularly preferred diamide compound is the compound F which is bis(methoxypropylamido)isodocosane and commercially available from Kao Corporation—Japan.

Concentration of diamide compound is in the range of 0.001 to 5%, preferably 0.002 to 3% more preferably 0.005 to 2% and most preferably 0.01 to 1% by weight calculated to total composition.

Additionally, one or more natural oil may be incorporated into the compositions of the present invention. Suitable are such as olive oil, almond oil, avocado oil, wheatgerm oil, ricinus oil or their mixture. Concentration of natural oil should be 0.01 to 2.5%, preferably 0.01. to 1%, more preferably 0.05 to 0.5% by weight, calculated to total each composition.

Compositions of the present invention can further comprise ingredients customarily found in such compositions such as alkalizing agents, preservatives antioxidants, fragrances, reducing agents and chelating agents.

The following example is to illustrate the present invention, but not to limit.

EXAMPLE 1

| Base composition | |
|---|---|
| | % by weight |
| Octyldodecanol | 1.3 |
| Cetearyl alcohol | 1.0 |
| Oleyl alcohol | 2.6 |
| Sodium lauryl sulphate | 1.0 |
| Xanthan gum | 1.0 |
| Sodium sulfite | 0.5 |
| Acetylcysteine hydrochloride | 0.4 |
| Toluene 2,5-diamine sulfate | 1.3 |
| m-aminophenol | 0.1 |
| Resorcinol | 0.4 |
| Tetrasodium EDTA | 0.2 |
| Fragrance, preservative | q.s |
| Ammonia 25% | 8.0 |
| Water | q.s. to 100 |

The above composition was stored for a period of up to 6 months and no instability was observed in terms of loss of colouring ability. Exclusion of either reducing agent resulted in loss of antioxidant activity and colouring effect was lost considerably.

EXAMPLE 2

Composition of example 1 was produced by addition of 0.1% by weight HC Red 3, a nitro direct dye and stored up to 3 months and no instability was observed in terms of loss of colouring ability. Exclusion of either reducing agent resulted in loss of antioxidant activity and colouring effect was lost considerably.

EXAMPLE 3

The composition of Example 1 was produced by replacing the two reducing agents as follows:

| | 3-a | 3-b | 3-c | 3-d | 3-e | 3-f |
|---|---|---|---|---|---|---|
| Sodium bisulfite | 0.5 | 0.5 | | | | |
| Sodium metabisulfite | | | 0.5 | 0.5 | | |
| Ammonium sulfite | | | | | 0.5 | 0.5 |
| Ammonium bisulfite | 0.2 | | 0.2 | | 0.2 | |
| Ammonium thioglycolate | | | | | | |
| Ammonium thiolactate | | | | | | |
| Cystein hydrochloride | | 0.4 | | 0.4 | | 0.4 |
| Cystamine hydrochloride | | | | | | |

| | 3-g | 3-h | 3-i | 3-j | 3-k | 3-l | 3-m |
|---|---|---|---|---|---|---|---|
| Sodium sulfite | | | | 0.3 | 0.4 | 0.2 | 0.1 |
| Sodium bisulfite | | 0.2 | | | | | |
| Sodium metabisulfite | | | 0.2 | | | | 0.4 |
| Ammonium sulfite | | | | | | 0.6 | |
| Ammonium bisulfite | 0.5 | 0.5 | 0.3 | | 0.1 | | |
| Ammonium thioglycolate | 0.2 | | | | 0.4 | | 0.4 |
| Ammonium thiolactate | | | | | | | |
| Cystein hydrochloride | | 0.4 | 0.3 | 0.1 | | 0.1 | |
| Cystamine hydrochloride | | | | | | | |
| Acetylcystein hydrochloride | | 0.2 | 0.4 | 0.1 | | 0.4 | 0.1 |

None of the compositions produced showed any instability after a storage period of up to 6 months measured as colouring ability of the compositions on hair.

The invention claimed is:

1. An oxidative dyeing composition comprising at least one oxidative dye precursor, comprising at least two structurally different reducing agents wherein the first is selected from inorganic reducing agents and present at a concentration of at least 0.1% by weight, calculated to the total composition, and the second is an organic reducing agent selected from thioglycolic acid, acetylcysteine and cysteine, and salts thereof, wherein the composition is substantially free of ascorbic acid and/or its salts, wherein the total concentration of inorganic and organic reducing agents does not exceed 5% by weight calculated to the total composition.

2. The composition according to claim 1 wherein the inorganic reducing agent is selected from ammonium bisulfite, ammonium sulfite, potassium metabisulfite, potassium sulfite, sodium hydrosulfite, sodium metabisulfite and sodium sulfite and their mixtures.

3. The composition according to claim 1, wherein the inorganic reducing agent is sodium sulfite.

4. The composition according to claim 1, wherein the organic reducing agent is acetylcysteine and/or its salts.

5. The composition according to claim 1, wherein the inorganic reducing agent is comprised at a concentration of 0.1 to 2.5% by weight calculated to total composition.

6. The composition according to claim 1, wherein the organic reducing agent is comprised at a concentration of 0.1 to 2.5% by weight calculated to total composition.

7. The composition according to claim 1, wherein the inorganic and organic reducing agents are comprised at a weight ratio of inorganic to organic reducing agents in the range of 20:1 to 1:5.

8. The composition according to claim 1, comprising at least one oxidative dyestuff precursor and at least one coupling agent.

9. The composition according to claim 1, comprising at least one direct dye.

10. The composition according to claim 1, wherein it is an aqueous composition and it is an emulsion.

11. A process for colouring keratin fibres especially human hair wherein a composition according to claim 1 is mixed with an oxidizing composition comprising at least one oxidizing agent, at a weight ratio in the range of 3:1 to 1:3 and is applied onto hair and is processed for 1 to 45 min at a temperature of 20 to 45° C. and rinsed off from hair.

12. A kit for oxidative colouring hair comprising at least two compositions wherein the one is a composition according to claim 1 and the other is a composition comprising at least one oxidizing agent.

13. The composition according to claim 1, wherein the salts are selected from ammonium thioglycolate, ethanolamine thioglycolate, sodium thioglycolate, potassium thioglycolate, magnesium thioglycolate, strontium thioglycolate, acetylcysteine hydrochloride, thioglycerine, and cysteine, hydrochloride and cystene, and salts thereof.

\* \* \* \* \*